US008471046B2

(12) United States Patent
List et al.

(10) Patent No.: US 8,471,046 B2
(45) Date of Patent: Jun. 25, 2013

(54) METHOD FOR PRODUCING CHIRAL α,β-EPOXY KETONES

(75) Inventors: Benjamin List, Mülheim an der Ruhr (DE); Corinna Reisinger, Zürich (CH); Xingwang Wang, Jiang Shu Province (CN)

(73) Assignee: Studiengesellschaft Kohle mbH, Muelheim an der Ruhr (DE)

( * ) Notice: Subject to any disclaimer, the term of this patent is extended or adjusted under 35 U.S.C. 154(b) by 226 days.

(21) Appl. No.: 12/920,877

(22) PCT Filed: Mar. 12, 2009

(86) PCT No.: PCT/DE2009/000315
§ 371 (c)(1),
(2), (4) Date: Sep. 3, 2010

(87) PCT Pub. No.: WO2009/112014
PCT Pub. Date: Sep. 17, 2009

(65) Prior Publication Data
US 2011/0009650 A1    Jan. 13, 2011

(30) Foreign Application Priority Data
Mar. 12, 2008    (DE) .................... 10 2008 013 962

(51) Int. Cl.
*C07D 301/12*    (2006.01)
(52) U.S. Cl.
USPC ....................................................... 549/531
(58) Field of Classification Search
USPC .................................................. 549/532, 531
See application file for complete search history.

(56) References Cited

U.S. PATENT DOCUMENTS
2008/0154036 A1    6/2008    Terada et al.

FOREIGN PATENT DOCUMENTS
WO    2005 077908 A1    8/2005

OTHER PUBLICATIONS

Balleste et al, Iron-Catalyzed Olefin Epoxidation inthe presence of Acetic acid: Insights into the Nature of Metal-Based Oxidant, J. Am. Chem. Soc. 2007, 129, p. 15964-15972.*
Ando et al, Sodium Percarbonate as a Hydrogen Peroxide Source for Organic Synthesis, Chemistry Letters, 1986, p. 665-666.*
Wang, et al; "Catalytic asymetric epoxidation of cyclic enones."; Journal of the American Chemical Society, May 14, 2008, vol. 130, No. 19, pp. 6070-6071 XP002534893.
Lattanzi; "Advances in asymmetric epoxidation of alpha, beta-unsaturated carbonyl compounds: The organocatalytic approach" Current Organic Synthesis, vol. 5, No. 2, May 2, 2008, pp. 117-133, XP009119114.
Potter et al; "Asymmetric epoxidation of electron-deficient olefins"; Chemical Communications 20000721 GB, No. 14, Jul. 21, 2000, pp. 12115-1225, XP002534894.
Genski, et al; "Epoxidation of electron deficient alkenes using tert-butyl hydroperoxide and 1,5,7-triazabicyclo[4.4,0] dec-5-ene and its derivatives": Synlett 1999 DE, No. 6, pp. 795-797, XP002534895 (tables 1-4).
McManus et al; "Enantiopure guanidine ases for enantioselective enone epoxidations: 1, Acylic guanidines" Synlett 2003 DE, No. 3, pp. 365-368, XP002534896, (table 1).
McManus et al; "Enantiopure guanidine bases for enantioselective enone epoxidations: 2, cyclic guanidines" Synlett 2003 DE, No. 3, pp. 369-371, XP002534896, (table 1).
Lattanzi; "Enantioselective epoxidation of alpha, beta-enones promoted by alpha, alpha, alpha-diphenyl-L-prolinol as bifunctional organocatalyst."; Organic Letters Jun. 23, 2005, vol. 7, No. 13, pp. 2579-2582, XP002534898 (table 1).
Lattanzi; "Bis/3,5-dimethylphenyl)-(S)-pyrrolidin-2-ylmethanol: an Improved Organocatalyst for the Asymmetric epoxidation of alpha, bata-enones"; Advanced Synthesis & Catalysis, vol. 348, 2006, pp. 339-346, XP002534899 (tables 1-3).
Li, et al; "4-Substituted-alpha, alpha-diaryl-proplinol s improve the enantioselective catalytic epoxidation of alpha, beta-enones." The Journal of Organic Chemistry, Jan. 5, 2007: vol. 72, No. 1, pp. 288-291, XP002534904 (tables 1,2).
Wang, et al; "Asymmetric counteranion-directed catalysis for the epoxidation of enals"; Angewandte Chemi (International Ed. in English) 2008, vol. 47, No. 6, Dec. 27, 2007, pp. 1119-1122, XP002534900.

* cited by examiner

*Primary Examiner* — Taylor Victor Oh
(74) *Attorney, Agent, or Firm* — Norris McLaughlin & Marcus, P.A.

(57) ABSTRACT

A process is claimed for the enantioselective epoxidation of α,β-unsaturated ketones, in which a compound of the general formula I,

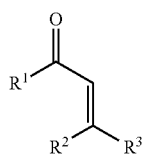

(I)

is reacted with an oxidizing agent to form α,β-epoxy ketones of the general formula II,

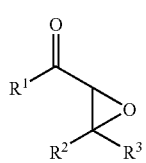

(II)

in which $R^1$, $R^2$, $R^3$ are as defined above. The α,β-epoxy ketones of the general formula II can be obtained in good yields and outstanding enantioselectivities from α,β-unsaturated ketones of the general formula I by epoxidation with hydrogen peroxide in the presence of a chiral catalyst, such as amino compounds and their acid addition salts.

11 Claims, No Drawings

METHOD FOR PRODUCING CHIRAL α,β-EPOXY KETONES

This application is a 371 of PCT/DE/2009/000315, filed Mar. 12, 2009, which claims foreign priority benefit under 35 U.S.C. §119 of the German Patent Application No. 10 2008 013 962.9 filed Mar. 12, 2008.

The present invention relates to a process for preparing chiral α,β-epoxy ketones.

Functionalized epoxides are very useful intermediates in the synthesis of industrially relevant compounds.

Possible routes to enantiomerically pure α,β-epoxy ketones include asymmetric epoxidations of the corresponding α,β-unsaturated ketones.

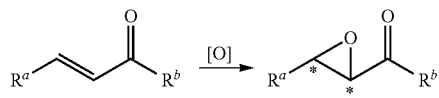

A series of examples of this type of reaction have been described in the literature. They include numerous examples of the enantioselective epoxidation of chalcone and chalcone derivatives. (Chem. Commun.) Highly enantioselective epoxidations of cyclic α,β-unsaturated ketones, however, are unknown. Neither with the aid of chiral reagents employed stoichiometrically, nor using chiral catalysts, has it been possible to achieve anything more than unsatisfactory enantioselectivities. Furthermore, there is no general method available for the highly enantioselective epoxidation of aliphatic α,β-unsaturated ketones.

It was an object of the present invention to provide a simple process for preparing enantiomerically enriched cyclic α,β-epoxy ketones.

The present invention provides a process for the enantioselective epoxidation of α,β-unsaturated ketones, in which a compound of the general formula I,

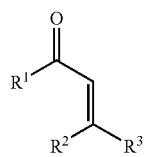

(I)

in which
$R^1$ is a branched or unbranched, saturated or unsaturated hydrocarbon radical having 1 to 30 carbon atoms, which may have suitable substituents and may have one or more heteroatoms in the chain,
$R^2$ is hydrogen, a branched or unbranched, saturated or unsaturated hydrocarbon radical having 1 to 30 carbon atoms, which may have suitable substituents and may have one or more heteroatoms in the chain, or an aryl group or heteroaryl group, which may have suitable substituents,
$R^3$ is hydrogen, a branched or unbranched, saturated or unsaturated hydrocarbon radical having 1 to 30 carbon atoms, which may have suitable substituents and may have one or more heteroatoms in the chain, or an aryl group or heteroaryl group, which may have suitable substituents,
$R^1$, $R^2$, and $R^3$ may be identical or different,
and the radical $R^1$ may, with the radicals $R^2$ and $R^3$, form a ring, which may have 5 to 20 members, be saturated or unsaturated, alicyclic or heteroalicyclic, and may have suitable substituents,
is reacted with an oxidizing agent to form α,β-epoxy ketones of the general formula II,

(II)

in which $R^1$, $R^2$, $R^3$ are as defined above.

It has been found that α,β-epoxy ketones of the general formula II are obtained in good yields and outstanding enantioselectivities from α,β-unsaturated ketones of the general formula I by epoxidation with hydrogen peroxide in the presence of a chiral catalyst, such as amino compounds and their acid addition salts.

The process of the invention is implemented by reacting α,β-unsaturated ketones of the general formula I with a suitable oxidizing agent in the presence of a chiral catalyst. Any catalyst can be used that supports the reaction between the α,β-unsaturated ketone and the oxidizing agent. Organic bases, more particularly amines and their acid addition salts, have proven particularly suitable. The addition salts can be used per se or may form in the course of the reaction. Preferred amines have a structure of the general formula III, $NH_2R^4$ in which
$R^4$ is a hydrocarbon group having 1 to 30 carbon atoms, such as a saturated or unsaturated, branched or linear alkyl group, alkenyl group, alkynyl group or aryl group, which may have suitable substituents including heteroatom substituents, or a heteroatom-containing hydrocarbon group, which may have suitable substituents, and their acid addition salts.

Preference is given to amines having the formula III, in which the radical $R^4$ has an additional basic functionality, such as an amino group.

The chiral catalyst is preferably selected from chiral amines of the general formula III, from addition salts of achiral amines of the general formula III with chiral acids, and from addition salts of chiral amines of the general formula III with achiral or chiral acids.

Examples of achiral acids which can be used in the process of the invention include halogenated carboxylic acids, such as halogenated acetic acids, e.g., trifluoroacetic acid, trichloroacetic acid, difluoroacetic acid and dichloroacetic acid, benzoic acid, substituted benzoic acids, etc.

Examples of suitable chiral acids are chiral organic phosphoric acids, phosphorimides, sulfuric acids, sulfonic acids, sulfonylimides, carboxylic acids, imides, etc. The chiral acids are preferably derived from binaphthol. In one possible embodiment, the chiral acid is selected from organic chiral phosphoric acids having the general formula IV,

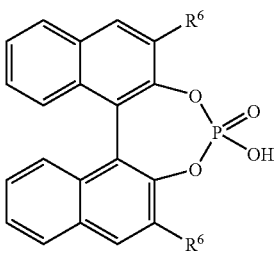

(IV)

in which
R⁶ is H, a hydrocarbon group, such as a saturated or unsaturated, branched or linear $C_1$-$C_{20}$ alkyl group, $C_2$-$C_{20}$ alkenyl group, $C_2$-$C_{20}$ alkynyl group or aryl group, which may have suitable substituents, including heteroatom substituents, or a heteroatom-containing hydrocarbon group, which may have suitable substituents.

The amine having the general formula III is preferably a primary amine. Particularly good results are obtained with amines which are selected from the following compounds having the formulae V, VI, and VII

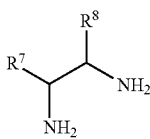

V

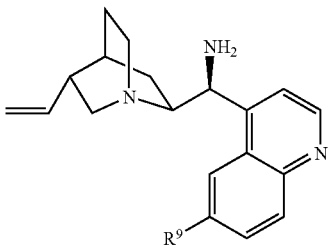

VI

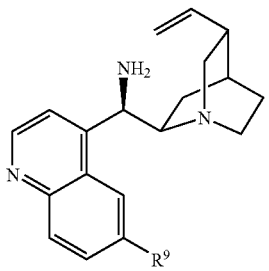

VII in which
$R^7$ is a hydrocarbon group, such as a saturated or unsaturated, branched or linear alkyl group, alkenyl group, alkynyl group or aryl group, which may have suitable substituents, including heteroatom substituents, or a heteroatom-containing hydrocarbon group, which may have suitable substituents, and
$R^8$ is a hydrocarbon group, such as a saturated or unsaturated, branched or linear alkyl group, alkenyl group, alkynyl group or aryl group, which may have suitable substituents, including heteroatom substituents, or a heteroatom-containing hydrocarbon group, which may have suitable substituents,
$R^7$ and $R^8$ may be identical or different, and the radicals $R^7$ and $R^8$ may form a ring, which may have 4 to 20 members, be saturated or unsaturated, alicyclic or heteroalicyclic, and may have suitable substituents, and $R^9$ is H, or a group —$OR^{10}$
in which $R^{10}$ is hydrogen, a hydrocarbon group having 1 to 30 carbon atoms, such as a saturated or unsaturated, branched or linear alkyl group, alkenyl group, alkynyl group or aryl group, which may have suitable substituents, including heteroatom substituents, or a heteroatom-containing hydrocarbon group, which may have suitable substituents.

The catalyst is used typically in an amount of 0.1 to 200 mol %, preferably of 1 to 30 mol %, based on the starting compounds.

The oxidizing agent is more particularly $H_2O_2$, which is used preferably in aqueous solution, more particularly in a concentration above 30% by weight, preferably between 30% and 50% by weight.

Hydrocarbon group in the context of the invention denotes a saturated or unsaturated, branched or linear alkyl group, alkenyl group, alkynyl group or aryl group, which may have suitable substituents, including heteroatom substituents, or a heteroatom-containing hydrocarbon group.

Alkyl may be unbranched (linear) or branched and has 1 to 30, preferably 1, 2, 3, 4, 5, 6, 7, 8, 9, 10, 11, 12, 13, 14, 15, 16, 17, 18, 19 or 20 carbon atoms. Alkyl is preferably methyl, but also ethyl, propyl, isopropyl, butyl, isobutyl, sec-butyl or tert-butyl, and also pentyl, 1-, 2- or 3-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, but preferably also, e.g. trifluoromethyl.

Alkyl is more preferably an alkyl having 1, 2, 3, 4, 5 or 6 carbon atoms, preferably methyl, ethyl, propyl, isopropyl, butyl, isopropyl, sec-butyl, tert-butyl, pentyl, hexyl, trifluoromethyl, pentafluoroethyl or 1,1,1-trifluoroethyl.

Cycloalkyl is preferably cyclopropyl, cyclobutyl, cyclopentyl, cyclohexyl or cycloheptyl. Alkylene is preferably methylene, ethylene, propylene, butylene, pentylene or hexylene, but also branched alkylene.

Alkylene is preferably vinyl.

Alkynyl is preferably C≡CH.

Halogen is F, Cl, Br or I.

Alkoxy is preferably methoxy, ethoxy, propoxy or butoxy.

$C_3$-$C_8$ heterocycloalkyl having one or more heteroatoms selected from N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or mono-, di-, tri-, tetra- or pentasubstituted.

Aryl is preferably phenyl, naphthyl or biphenyl.

Arylalkyl is preferably benzyl.

Heteroaryl having one or more heteroatoms selected from N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, and also preferably 1,3-benzodioxol-5-yl, 1,4-benzodioxan-6-yl, 2,1,3-benzothiadiazol-4- or -5-yl or 2,1,3-benzoxadiazol-5-yl.

Examples of substituents are $C_1$-$C_4$ alk(en)yl, aryl, heteroaryl, halogen, such as F, Cl, Br, I, $NO_2$, amino, etc.

The reaction can be carried out in typical polar or nonpolar organic solvents.

EXAMPLES

A. General Instructions:

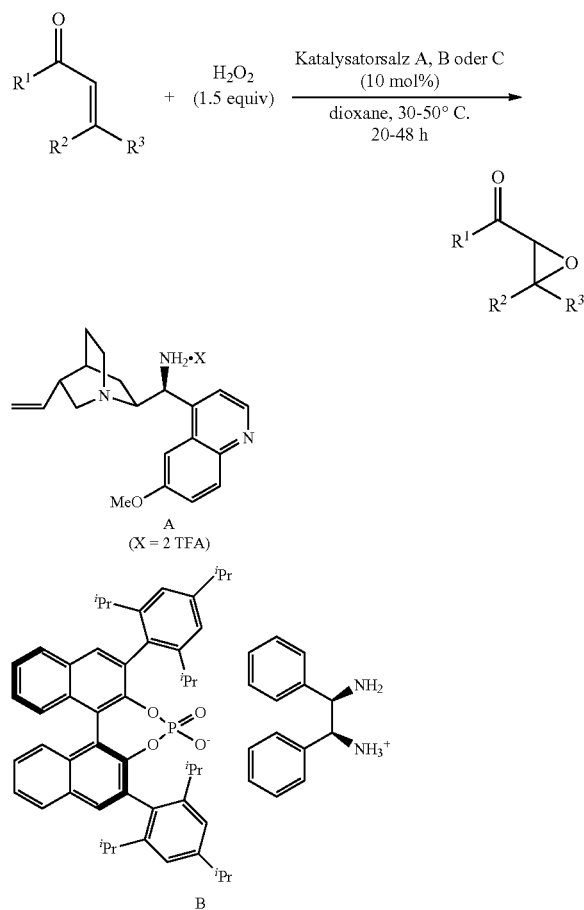

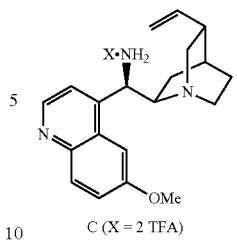

C (X = 2 TFA)

The catalyst salts A-C were prepared in situ in dioxane (2-4 ml) from the amine (10 mol %) and the respective acid (10-20 mol %). After 20 minutes of stirring the α,β-unsaturated ketones were added, and after a further 20 minutes, 1.5 equivalents of an aqueous hydrogen peroxide solution (50% w/w) were added. After a reaction time of 20-72 h at 30-50° C., the reaction mixture was cooled and water added. This was followed by extraction with ether, after which the combined organic phases were washed with saturated sodium chloride solution, dried ($Na_2SO_4$), filtered and concentrated on a rotary evaporator, to give the crude products which were purified by chromatography ($SiO_2$, ether/pentane). In the case of the acyclic α,β-unsaturated ketone, the crude product obtained in this way was stirred optionally for 10 minutes to 1 hour in ether with one equivalent of 1 N NaOH solution. Thereafter the ether phase was washed with saturated sodium chloride solution, dried ($Na_2SO_4$), filtered and concentrated on a rotary evaporator. This was followed by purification by chromatography ($SiO_2$, ether/pentane).

With Catalyst A:
1.0 mmol scale based on the α,β-unsaturated ketone. The catalyst salt A was prepared from 9-amino-9-deoxyepiquinine (8.1 mg, 0.1 mmol, 10 mol %) and TFA (15.3 µl, 0.2 mmol, 20 mol %).

With Catalyst B:
0.5 mmol scale based on the α,β-unsaturated ketone. The catalyst salt B was prepared from (R,R)-DPEN (10.6 mg, 0.05 mmol, 10 mol %) and S-TRIP (37.6 mg, 0.05 mmol, 10 mol %).

With Catalyst C:
1.0 mmol scale based on the α,β-unsaturated ketone. The catalyst salt C was prepared from 9-amino-9-deoxyepiquinidine (8.1 mg, 0.1 mmol, 10 mol %) and TFA (15.3 µl, 0.2 mmol, 20 mol %).

TABLE I

Preparation of cyclic epoxides

| Example | Epoxide | Catalyst | Yield (%) | er |
|---------|---------|----------|-----------|------|
| 1 | | B | 98 | 96:4 |
| 2 | (cyclohexanone epoxide) | A | 91 | 3:97 |
| 3 | (4,4-dimethylcyclohexanone epoxide) | B | 80 | 97:3 |

TABLE I-continued

Preparation of cyclic epoxides

| Example | Epoxide | Catalyst | Yield (%) | er |
|---|---|---|---|---|
| 4 | 4,4-dimethyl cyclohexanone epoxide | B | 76 | 98:2 |
| 5 | 3,5,5-trimethyl cyclohexanone epoxide | B | 63 | 96:4 |
| 6 | 1-methyl cyclohexanone epoxide | A | 70 | 98:2 |
| 7 | 1-ethyl cyclohexanone epoxide | A | 73 | 98.5:1.5 |
| 8 | 1-isopropyl cyclohexanone epoxide | A | 79 | 99:1 |
| 9 | 1-isobutyl cyclohexanone epoxide | A | 73 | 98:2 |
| 10 | 1-(2-phenylethyl) cyclohexanone epoxide | A | 84 | 98.5:1.5 |
| 11 | 1-benzyl cyclohexanone epoxide | A | 78 | 99:1 |
| 12 | 1-benzyl cyclohexanone epoxide | C | 77 | 98.5:1.5 |
| 13 | 3,3,1-trimethyl cyclohexane-1,2-dione epoxide | A | 49 | 96:4 |
| 14 | cycloheptanone epoxide | B | 82 | 99:1 |
| 15 | 1-ethyl cycloheptanone epoxide | A | 82 | >99.5:0.5 |
| 16 | 1-benzyl cycloheptanone epoxide | A | 85 | >99.5:0.5 |
| 17 | cyclopentanone epoxide | B | 29 | 89:11 |

TABLE 2

Preparation of alicyclic epoxides

| Example | R¹ | R² | R³ | Catalyst | Yield (%) | er |
|---|---|---|---|---|---|---|
| 18 | $nC_6H_{13}$ | H | Me | A | 72 | 98.5:1.5 |
| 19 | CH₂CH₂Ph (branched) | H | Me | A | 85 | 98.5:1.5 |

TABLE 2-continued

Preparation of alicyclic epoxides

| Example | R¹ | R² | R³ | Catalyst | Yield (%) | er |
|---|---|---|---|---|---|---|
| 20 | ⸺CH(CH₃)CH₂CH₂Ph | Me | H | A | 82 | 97.5:2.5 |
| 21[a] | ⸺CH(CH₃)CH₂CH₂Ph | H | Me | C | 90 | 95:5 |
| 22 | ⸺CH(CH₃)CH₂CH=CH₂ | H | Me | A | 76 | 98.5:1.5 |
| 23 | iBu | H | Me | A | 77 | 98.5:1.5 |
| 24 | Cy | H | Me | A | 83 | 98.5:1.5 |
| 25 | 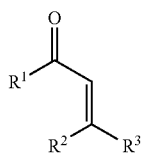 tBu | H | Me | A | 81 | >99.5:0.5 |
| 26 | Me | H | Et | A | 55 | 98.5:1.5 |
| 27 | nC₉H₁₉ | H | Et | A | 82 | 99:1 |
| 28 | nC₅H₁₁ | H | nC₅H₁₁ | A | 76 | 99:1 |
| 29 | nC₅H₁₁ | H | iBu | A | 81 | 98.5:1.5 |

[a] with catalyst C the opposite enantiomer is obtained.

The invention claimed is:

1. A process for the enantioselective epoxidation of α,β-unsaturated ketones, said process comprising reacting a compound of the formula I, (I)

in which
R¹ is a branched or unbranched, saturated or unsaturated hydrocarbon radical having 1 to 30 carbon atoms, which is substituted or unsubstituted and may have one or more heteroatoms in the chain,
R² is hydrogen, a branched or unbranched, saturated or unsaturated hydrocarbon radical having 1 to 30 carbon atoms, which is substituted or unsubstituted and may have one or more heteroatoms in the chain, or an aryl group or heteroaryl group, which is substituted or unsubstituted,
R³ is hydrogen, a branched or unbranched, saturated or unsaturated hydrocarbon radical having 1 to 30 carbon atoms, which is substituted or unsubstituted and may have one or more heteroatoms in the chain, or an aryl group or heteroaryl group, which is substituted or unsubstituted,
R¹, R², and R³ may be identical or different,
and the radical R¹ may, with the radicals R² and R³, form a ring, which may have 5 to 20 members, be saturated or unsaturated, alicyclic or heteroalicyclic, and is substituted or unsubstituted,
with an oxidizing agent to form a 3-epoxy ketone of the formula II, (II)

in which R¹, R², R³ are as defined above,
wherein said reacting is carried out in the presence of a chiral catalyst, said chiral catalyst is selected from the group consisting of amines and their acid addition salts, and said amines have the formula III:

NH₂R⁴ in which
R⁴ is an optionally substituted hydrocarbon group having 1 to 30 carbon atoms, or an optionally substituted, heteroatom-containing hydrocarbon group, and their acid addition salts.

2. The process as claimed in claim 1, wherein the oxidizing agent is selected from hydrogen peroxide, alkyl peroxides, sodium hypochlorite, peracids, iodoso compounds and borates.

3. The process as claimed in claim 2, wherein an aqueous hydrogen peroxide solution is used as oxidizing agent.

4. The process as claimed in claim 1, wherein the chiral catalyst is selected from chiral amines of the formula III, from addition salts of achiral amines of the formula III with chiral acids, and from addition salts of chiral amines of the formula III with achiral or chiral acids.

5. The process as claimed in claim 4, wherein the chiral acids are selected from chiral organic phosphoric acids, phosphorimides, sulfuric acids, sulfonic acids, sulfonylimides, carboxylic acids, and imides.

6. The process as claimed in claim 5, wherein the chiral acid is derived from binaphthol.

7. The process as claimed in claim 6, wherein the chiral acid is selected from organic chiral phosphoric acids having the formula IV,

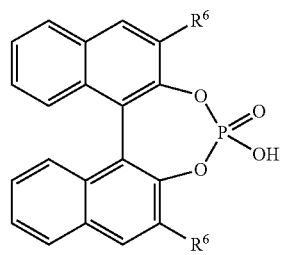

in which
R⁶ is H, an optionally substituted hydrocarbon group, or an optionally substituted, heteroatom-containing hydrocarbon group.

8. The process as claimed in claim 1, wherein the amine having the formula III is a primary amine.

9. The process as claimed in claim 8, wherein the primary amine is selected from compounds having the formulae V, VI and/or VII

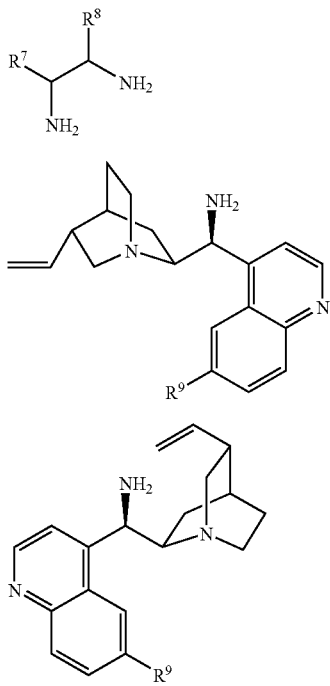

in which

R⁷ is an optionally substituted hydrocarbon group, or an optionally substituted, heteroatom-containing hydrocarbon group, and R⁸ is an optionally substituted hydrocarbon group, or an optionally substituted, heteroatom-containing hydrocarbon group, R⁷ and R⁸ may be identical or different, and the radicals R⁷ and R⁸ may form a ring, which may have 4 to 20 members, be saturated or unsaturated, alicyclic or heteroalicyclic, and is substituted or unsubstituted, and R⁹ is H, or a group —OR¹⁰ in which

R¹⁰ is hydrogen, an optionally substituted hydrocarbon group having 1 to 30 carbon atoms, or an optionally substituted, heteroatom-containing hydrocarbon group.

10. The process as claimed in claim 1, wherein "substituted" means substitution by one or more substituents selected from the group consisting of $C_1$-$C_4$-alkyl, $C_1$-$C_4$-alkenyl, aryl, heteroaryl, halogen, $NO_2$ and amino.

11. The process as claimed in claim 7, wherein R⁶ is an unsubstituted or substituted, saturated or unsaturated, branched or linear $C_1$-$C_{20}$-alkyl group, $C_2$-$C_{20}$-alkenyl group, $C_2$-$C_{20}$-alkynyl group or aryl group.

* * * * *